United States Patent [19]

Porter

[11] Patent Number: 5,578,291

[45] Date of Patent: Nov. 26, 1996

[54] METHOD AND COMPOSITION FOR OPTIMIZING LEFT VENTRICULAR VIDEOINTENSITY IN ECHOCARDIOGRAPHY

[75] Inventor: Thomas R. Porter, Omaha, Nebr.

[73] Assignee: The Board of Regents of the University of Nebraska, Lincoln, Nebr.

[21] Appl. No.: 301,146

[22] Filed: Sep. 6, 1994

Related U.S. Application Data

[63] Continuation of Ser. No. 113,415, Aug. 27, 1993, abandoned, which is a continuation-in-part of Ser. No. 57,298, May 14, 1993, abandoned.

[51] Int. Cl.⁶ .................................................. A61K 49/00
[52] U.S. Cl. ................................................................. 424/9.5
[58] Field of Search ..................... 424/9, 9.5; 128/662.02; 536/4.1; 514/2

[56] References Cited

FOREIGN PATENT DOCUMENTS 9205806  4/1992  WIPO .

OTHER PUBLICATIONS

CA102(12):100841t, "Ultrasound Contrast Agent", Rasor et al.. DE 3,324,754 Jan. 17, 1985.

Medline Abstract #90376405, "On the applization of ultrasonic contrast agents for blood flowmetry & assessment of cardiac perfusion," Bleeker et al, J Ultrasound Med, Aug. 1990 p. 461.

*Primary Examiner*—José G. Dees
*Assistant Examiner*—Mary C. Cebulak
*Attorney, Agent, or Firm*—Zarley, McKee, Thomte, Voorhees & Sease

[57] ABSTRACT

This invention provides a new ultrasound contrast agent which is safe and can reach the left side of the heart in adequate amounts to determine blood flow to the muscle of the heart. The contrast agent comprises a simple sonicated mixture of a protein the body normally makes (albumin) combined with a naturally occurring sugar (dextrose). This mixture upon sonication contains small bubbles (microbubbles) and can be used following an intravenous injection to study blood flow to the muscle of the heart (myocardium) without the need of invasive catheters or radiation. In another embodiment, there is provided an inexpensive test to study blood flow in the heart using echocardiography, thus avoiding the more expensive nuclear procedures that are presently employed to determine blood flow in the heart muscle, and eliminating the risk of radiation.

12 Claims, No Drawings

METHOD AND COMPOSITION FOR OPTIMIZING LEFT VENTRICULAR VIDEOINTENSITY IN ECHOCARDIOGRAPHY

BACKGROUND OF THE INVENTION

This is a continuation of application Ser. No. 08/113,415 filed on Aug. 27, 1993, abandoned, which is a continuation-in-part of Ser. No. 08/057,298 filed May 19, 1993, abandoned, A METHOD AND COMPOSITION FOR OPTIMIZING VIDEOINTENSITY IN ULTRASONIC IMAGING AND ECHOCARDIOGRAPHY, filed by Thomas R. Porter on May 14, 1993, and assigned to the same assignee as this application.

This invention relates to an improved ultrasonic imaging and echocardiographic methodology and to novel contrast agents for use therein, as well as to the production of these agents.

Ultrasonic imaging is used as a diagnostic tool to aid in therapeutic procedures. For example, contrast echocardiography has been used to delineate intracardiac structures, assess valvular competence, and demonstrate intracardiac shunts.

A multiplicity of potential agents has been reported for contrast echocardiography. Though there have been many reports of transpulmonary transmission, it is believed that no agent currently in clinical use routinely attains left heart contrast after intravenous injection. Development of standardized echo contrast agents containing uniformly small and stable gaseous microbubbles enabling reliable left heart contrast is an important prerequisite for further progress in the newly developing field of myocardial contrast echo imaging.

In order for ultrasound contrast agents to non-invasively determine myocardial perfusion following an intravenous injection, they must first pass reliably through the pulmonary circulation into the left ventricular chamber. An important object of this invention is to provide such contrast agents and methods for their production in dosage forms suitable for human diagnostic use, not only by the cardiologist, but also by other specialties which may wish to employ such contrast agents for other types of ultrasonic imaging.

SUMMARY OF THE INVENTION

In accordance with this invention, there is provided an ultrasound contrast agent comprising a sonicated solution containing human serum albumin and a pharmaceutically acceptable saccharide. Dextrose, which is readily available in pharmaceutically acceptable dosage forms, is exemplary of such saccharides.

In preferred embodiments, the contrast agents of this invention exhibit microbubble concentrations greater than about $4 \times 10^8$/ml. Such concentrations are believed to be unique and critical to obtaining the equally unique echocardiographic properties demonstrated hereinafter. Consequently, highly preferred is an echocardiographic contrast agent comprising a sonicated mixture of between about a three-fold and about a ten-fold dilution of human serum albumin with aqueous dextrose, said contrast agent being in a pharmaceutically effective dosage form and having a microbubble concentration of greater than about $4 \times 10^8$/ml.

Generally, for echocardiographic applications the contrast agent of this invention is formulated in a pharmaceutically effective dosage form for either intravenous or intracoronary administration to a human subject. Thus, another embodiment of this invention is a sonicated ultrasound contrast agent in a pharmaceutically acceptable dosage form for injection into a human subject comprising a sonicareal multifold dilution of albumin with a pharmaceutically acceptable aqueous saccharide capable of producing a microbubble concentration of greater than about $4.5 \times 10^8$/ml and a Peak Videointensity (as defined hereinafter) of at least about 50% above baseline.

Exemplary of the saccharide solutions of this invention are an aqueous monosaccharide solution (e.g. having the formula $C_6H_6O_{12}$, such as, the hexoses, dextrose or fructose, or mixtures thereof), aqueous disaccharide solution (e.g., having the formula $C_{12}H_{22}O_{11}$, such as sucrose, lactose or maltose, or mixtures thereof), or aqueous polysaccharide solution (e.g., soluble starches having the formula $(C_6H_{10}O_5)_n$, wherein n is a whole integer between about 20 and about 200, such as amylose or dextran, or mixtures thereof.

In general, for such dosage forms a sonicated mixture of commercially available albumin (human), USP, solution (generally supplied as 5% or a 25%, by weight, sterile aqueous solutions) and commercially available dextrose, USP, for intravenous administration are employed. (Generally, USP dextrose is commercially available as 5% up to 70%, by weight, aqueous solutions; 50% dextrose, injection, USP being preferred). In a preferred embodiment of this invention a multifold dilution of aqueous albumin with between about 5% and about 50% by weight of aqueous dextrose solution is employed. Excellent results have been achieved when the contrast agent is sonicated (in accordance with the procedures hereinafter described) for at least about 80 seconds.

Another embodiment of this invention is a contrast agent consisting essentially of a sonicated mixture of about a three-fold to about a four-fold dilution of sterile human serum albumin, preferably a commercially available 5% by weight aqueous solution, with about 50% by weight aqueous dextrose, said contrast agent being in a pharmaceutically effective dosage form for intravenous or intracoronary injection.

Upon peripheral venous administration of the contrast agents of this invention to a subject to determine left ventricular videointensity by echocardiography, optimization of the left ventricular videointensity is attained. Thus, another embodiment of this invention relates to an improved method for determining left ventricular videointensity by echocardiography. The improvement comprises replacing the contrast agents currently administered to the subject of the echocardiography with a novel contrast agent of this invention. This results in optimization of the left ventricular videointensity. Although various methods of administration are currently employed in conventional echocardiography, intravenous administration, using a pharmaceutically effective dosage form for intravenous administration, is preferred. In accordance with this invention, peripheral venous administration in such dosage form is especially preferred.

The contrast agents of this invention, using a mixture containing suitable quantities of albumin and dextrose and sonicated in accordance with the methods of this invention, produce the critical microbubble concentrations discussed hereinbefore and result in significantly improved transpulmonary passage and left ventricular chamber uptake, when compared with a similar sample of sonicated albumin alone. This has three very important clinical implications. First, by improving left ventricular uptake compared to sonicated albumin alone, the albumin/dextrose combination improves the possibility of detecting myocardial uptake and perfusion from an intravenous injection. The new ultrasound contrast agents of this invention, therefore, enable echocardiography to quantify myocardial perfusion analogous to state of the art nuclear imaging, but without the need for radiation. Secondly, the use of certain dextrose percentages allows for administration of the mixture either by intravenous or by intracoronary pathways. Thirdly, the use of dextrose solutions to dilute scarce and expensive human serum albumin, reduces contrast agent cost.

The contrast agents of this invention can be produced by first preparing a solution of human serum albumin diluted with a dextrose solution. Thereafter, small and persistent contrast agent microbubbles are produced. These bubbles appear to be the source of the echo contrast effect. Thus, the method employed for producing these bubbles must be capable of producing bubbles of sufficiently small size to pass through the microvasculature, yet large enough to permit effective echocardiographic visualization of the left ventricular myocardium.

In one embodiment, the microbubbles are produced by sonication under conditions which optimize left ventricular videointensity. In general, and as discussed more fully hereinafter, sonication conditions which produce concentrations of greater than about $4\times10^8$/ml of between about 3 and about 5 micron microbubbles are preferred, e.g., see U.S. Pat. No. 4,572,203, U.S. Pat. No. 4,718,433 and U.S. Pat. No. 4,774,958, the contents of each of which are incorporated herein by reference.

Intravenous injections of sonicated albumin (Albunex®, Molecular Biosystems, Circulation 1992;86:I-524) have resulted in left ventricular chamber ultrasound videointensity in 80% of cases. Because these microbubbles are destroyed as they pass through the pulmonary capillaries, the concentration of microbubbles that reach the left ventricle is less than the right ventricle, and the stability of the microbubble in the left ventricular cavity is reduced. If a high concentration of these microbubbles can reach the left ventricular chamber, however, enough numbers of microbubbles will reach the coronary circulation to determine myocardial blood flow with contrast echocardiography.

Recent evidence in animals has shown that a 1:1 dilution of albumin with 50% dextrose prior to sonication results in more reliable and increased transpulmonary passage of microbubbles. The mechanism responsible for this is unknown.

In addition, using sonicated dextrose alone does not produce a stable small microbubble solution. Although dextrose appears to be the correct diluting agent, it is unclear what ratio the dilution should be in order to achieve maximal transpulmonary passage. An object of this invention is to provide the dilution of sonicated albumin with 50% dextrose which produces maximal left ventricular videointensity following intravenous injections.

Sonicated albumin can be used following intracoronary injections to detect coronary blood flow reserve in humans, and determine whether angiographically successful coronary angioplasty in humans results in improved anterograde coronary blood flow reserve. Intravenous sonicareal albumin, however, may have limited clinical applications because of variable transpulmonary passage into the left ventricle during systole.

Improving the transpulmonary passage of sonicated albumin is important to pursue for three reasons. First, it has been found that sonicated albumin alone does not result in consistent transpulmonary passage and subsequent left ventricular uptake. In order to detect myocardial perfusion, a large concentration of albumin microbubbles must reach the left ventricular cavity. Secondly, the albumin microbubbles from sonicated albumin alone which reach the left ventricular cavity are unstable, and actually lose their videointensity in systole when left ventricular pressure is increased. The microbubbles which reach the left ventricular cavity must be stable enough to withstand the naturally occurring pressures within the left ventricular cavity. Thirdly, 5% human albumin is expensive and limited in availability. Thus, the diluted contrast agents of this invention, which provide consistently improved transpulmonary passage, result in an ultrasound contrast agent which is a less expensive agent to produce.

As will be discussed hereinafter, in accordance with this invention, it has been found that an approximately three-fold to seven-fold dilution of albumin with dextrose, with an extended sonication time, results in the best left ventricular videointensity of any of the contrast agents investigated to date.

DETAILED DESCRIPTION OF THE INVENTION

Sonicated albumin has been used to study coronary flow reserve and immediate post-angioplasty anterograde blood flow reserve in humans. In humans without significant coronary artery disease, left main coronary artery injections of sonicated albumin before and after intracoronary papaverine result in time intensity curves which can be utilized to determine coronary flow reserve. It has been demonstrated that the washout of ultrasound contrast from the human myocardium in this setting correlates with coronary flow reserve measured by more invasive techniques.

Secondly, intracoronary sonicated albumin injections in humans with coronary artery disease, before and after angioplasty, has been done. The functional reserve of the myocardium supplied by the vessel undergoing angioplasty is immediately improved following angioplasty. The degree of improvement depends not on how visually successful the angioplasty was, but on how quantitatively successful the improvement in stenosis area was after angioplasty.

These intracoronary injections of sonicated albumin provide important information about myocardial blood flow and the collateral circulation of the heart, but require invasive technology to deliver the ultrasound contrast agent. Sonicated albumin does not reliably cross the pulmonary circulation into the left ventricular chamber following an intravenous injection, and thus at present cannot be used to non-invasively detect myocardial blood flow.

Examples 4–6 demonstrate the effect of various dilutions of sonicated albumin (human) USP, 5% solution with dextrose Injection USP, 50% on ultrasound videointensity in vitro and in healthy volunteers. Example 7 demonstrates the effect of various dilutions of sonicated albumin with dextrose in human volunteers with known cardiac disease.

In all the following examples all parts and percentages are by weight, unless stated otherwise. All dilutions are by volume.

EXAMPLE 1

Preparation of sonicated albumin and sonicated albumin/dextrose solutions for Examples 4–5.

Albumin (human) USP, 5% solution (hereinafter referred to in this example as "Albumin"), was obtained from a commercial source. Eight milliliter aliquots of pure Albumin, Albumin diluted 1:1, 1:3, and 1:7 with dextrose Injection USP, 50% (hereinafter referred to in this example as "Dextrose") are placed in 12.0 cc syringes. A commercially available sonicator (Heat Systems Ultrasonics Corp.; Model XL-1010) was used to create microbubbles. The sonication technique was that of Keller et al (see J Am Coll Cardiol 1988;12:1039–47) which involves placing the sonicating horn just at or near the surface of the Albumin or Albumin/Dextrose mixture and applying continuous sonication at 20,000 Hz and a power output of 210W for 40 seconds.

EXAMPLE 2

Preparation of sonicated albumin and sonicated albumin/dextrose solutions for Example 6.

Albumin was diluted one-fold (1:1), three-fold (1:3), and seven-fold (1:7) and sonicated for 40 seconds, while another three-fold (1:3 L) and seven-fold (1:7 L) dilutions were sonicated for 80 seconds. For dilutions sonicated for 40 seconds, 8 milliliters of pure albumin or albumin dilution were placed in 12 cc syringes. For the dilutions sonicated for 80 seconds (1:3 L and 1:7 L), 16 milliliters of the dilution were placed in a 35 milliliter plastic syringe. The sonication technique used to create microbubbles was that of Keller et al (supra).

EXAMPLE 3

Preparation of sonicated albumin and sonicated albumin/dextrose solutions for Example 7.

Commercially available 5% albumin was diluted with 50% dextrose (d50)(1:1) and sonicated for 70 seconds while three-fold (1:3 d50)and four-fold (1:4 d50)dilutions were sonicated for 80 seconds. Additionally, 5% albumin was diluted with 5% dextrose (d5) three-fold (1:3 d5 and 1:4 d5) and sonicated for 80 seconds. 16.0 Milliliters of all dilutions were placed in 35 cc syringes, and then sonicated. The four-fold albumin dilution with 50% dextrose was concentrated by allowing 32.0 milliliters of the solution to settle and then decanting the clear layer. This results in a 5.0 milliliter bolus injection of highly concentrated microbubbles (1:4 d50C).

All solutions were then immediately stored in a sterile container and used within 24 hours. All samples were prepared in a sterile laminar flow room. Microbubble size was assessed using hemocytometry and microbubble concentration was assessed using a Model ZBI Coulter Counter (Coulter Electronics, Hialeah, Fla.).

EXAMPLE 4

The effects of 50% dextrose on sonicated albumin: flow cell study.

Using an acrylic chamber (50 milliliter volume) connected to a flow system operating at 100 milliliters/minute, 87 injections (0.05 milliliters over 1 second) of six different samples of sonicated albumin and sonicated albumin diluted with 50% dextrose were bolus injected proximal to a mixing chamber. After mixing, the microbubbles flowed through the acrylic chamber which was scanned with a 3.5 Megahertz transducer. The samples tested were (1) sonicated albumin alone (SA), (2) 1:1 dilution of albumin with 50% dextrose prior to sonication (SA/D50 1:1 P), (3) 1:7 dilution of albumin with 50% dextrose prior to sonication (SA/D50 1:7 P), (4) 1:1 dilution of albumin with 50% dextrose after sonicating albumin alone (SA/D50 1:1 A), and (5) dilution of albumin with 50% dextrose after sonicating albumin (SA/D50 1:7A). Videointensity in the acrylic chamber was plotted as a function of time following each bolus injection using on-line software available through a commercially available ultrasound system (Hewlett Packard 1500, Andover, Mass.). The peak videointensity, area under the time intensity curve, half time of ultrasound contrast washout from peak intensity (half time), and mean transit time were plotted and compared between the five samples. Two of the six samples were analyzed for microbubble size and concentration using hemocytometry.

Table 1 demonstrates that there were no significant differences in area under the curve, peak videointensity, or mean transit times between SA/D50 1:1 P or SA/D50 1:7 P when compared to SA. The addition of 50% dextrose after sonication (SA/D50 1:1 A and SA/D50 1:7 A), however, did result in a significant decrease in peak videointensity and area under the time intensity curve.

TABLE 1

| Time Intensity Curve Parameter | D50 SA 1:1S | D50 SA 7:1S | D50 SA 1:1UN | D50 SA 7:1UN |
| --- | --- | --- | --- | --- |
| AREA | | | | |
| MEAN | 98 | 94 | 75 | 53 |
| STD | 20 | 24 | 19 | 23 |
| PEAK INTENSITY | | | | |
| MEAN | 105 | 94 | 83 | 55 |
| STD | 17 | 28 | 6 | 12 |
| MEAN TRANSIT TIME | | | | |
| MEAN (seconds) | 99 | 109 | 92 | 94 |
| STD | 14 | 18 | 25 | 27 |

Difference in time intensity curve parameters (expressed as percent of sonicated albumin alone) in a flow cell between dilutions of albumin with 50% dextrose prior to sonication and after sonication. Abbreviations: D50 SA 1:1P = albumin mixed 1:1 with dextrose prior to sonication; D50 SA 7:1P = one part albumin mixed with seven parts dextrose prior to sonication; D50 SA 1:1UN = albumin mixed 1:1 with dextrose after sonicating albumin alone; D50 SA 7:1UN = one part albumin mixed with seven parts dextrose after sonicating albumin alone. STD = standard deviation.

Two of the seven sonicated samples were analyzed for microbubble size and density using hemocytometry. There was a similar concentration of microbubbles which were greater than three microns for SA($1.50 \times 10^8$ microbubbles/milliliter), SA/D50 1:1P($1.68 \times 10^8$ microbubbles/milliliter) and SA/D50 1:7 P($1.34 \times 10^8$ microbubbles/milliliter). There were fewer microbubbles less than three microns in the SA/D50 1:7 P compared to SA/D50 1:1 P and SA($0.1 \times 10^8$/milliliter SA/D501:7P compared to $1.7 \times 10^8$/milliliter SA and $1.1 \times 10^8$/ milliliter SA/D50 1:1). One sample of the SA/D50 1:1 A and SA/D50 1:7A(50% dextrose added after sonication of albumin) were analyzed in a similar manner, and showed significantly fewer microbubbles greater than three microns in size($0.8 \times 10^8$ microbubbles/milliliter for SA/D50 1:1 A and $0.1 \times 10^8$ microbubbles/milliliter for SA/D50 1:7 A).

These data suggest that diluting albumin up to seven-fold prior to sonication results in no significant loss in peak videointensity and area under the curve. This preservation of ultrasound videointensity following large dilutions is only seen when 50% Dextrose is sonicated with albumin, and not added after sonication. The seven-fold dilution with 50% dextrose results in significantly fewer microbubbles less than three microns. This did not decrease the videointensity of this solution compared to sonicated albumin alone.

EXAMPLE 5

Effects of diluting albumin with 50 % dextrose in humans.

Three consecutive 8.0 milliliter intravenous injections of incremental dilutions of sterile sonicated solutions of albumin with 50% dextrose (1:1, 1:3, and 1:7 albumin:dextrose), as well as sonicated albumin (SA), alone were given to 14 healthy volunteers. Following each injection, left ventricular uptake was quantified by measuring area under the time intensity curve from the mid-left ventricular cavity using on-line digitally acquired videointensity obtained from software supplied in conjunction with the commercially available Hewlett Packard Sonos 1500 Phased Array imaging system (Hewlett Packard, Andover, Mass.). The results are shown in Table 2.

TABLE 2

| Parameter | SA | 1:1 | 1:3 | 1:7 |
| --- | --- | --- | --- | --- |
| AREA | 48 ± 51 | 79 ± 44 | 64 ± 42 | 105 ± 61* |
| PEAK INTENSITY | 3.25 ± 2.4 | 5.1 ± 2.2 | 3.9 ± 1.9 | 5.6 ± 2.4* |

*$P < 0.05$ compared to SA, ANOVA.

One of the three dilutions resulted in improved left ventricular uptake compared to SA in 13 of the 14 volunteers. The 1:7 dilution produced the maximum uptake in 8 of the 14 volunteers. There were no adverse effects in any of the volunteers to any of the injections. Blood pressure and heart rate did not change in response to any dilution. These responses demonstrate that a seven-fold dilution of albumin with dextrose produces the best transpulmonary passage and maximal left ventricular videointensity.

EXAMPLE 6

Effects of extended sonication time on transpulmonary passage of dextrose solutions.

Intravenous injections of incremental dilutions of sterile sonicated 5% human serum albumin with 50% dextrose (1:1, 1:3, 1:7, 1:3 L, 1:7 L), as well as sonicated albumin (SA) alone, were given to 10 healthy human volunteers. Following each injection, the peak left ventricular videointensity (PVI), area under the time intensity curve (Area), and mean transit time (MTT) of microbubbles through the cavity were measured. Videointensity was plotted as a function of time using on-line digitally acquired videointensity obtained from software supplied in conjunction with the commercially available Hewlett Packard Sonos 1500 Phased Array imaging system (Hewlett Packard, Andover, Mass.). The results are shown in Table 3.

TABLE 3

| Agent | Microbubble concentration ($\times 10^8$/ml) | Microbubble size (microns) | PVI | Area | MTT (seconds) |
| --- | --- | --- | --- | --- | --- |
| SA | 3.5 ± 0.7 | 4.7 ± 0.2 | 2.5 ± 2.4 | 28 ± 25 | 10.2 ± 2.6 |
| 1:1 | 2.1 ± 0.8* | 5.5 ± 0.4 | 5.5 ± 5.9 | 75 ± 81 | 12.9 ± 3.6* |
| 1:3 | 2.1 ± 0.8* | 5.6 ± 0.1* | 5.6 ± 3.8 | 74 ± 63 | 13.1 ± 4.6* |
| 1:7 | 1.4 ± 0.9* | 6.2 ± 0.5* | 3.7 ± 3.8 | 53 ± 54 | 13.1 ± 4.8* |
| 1:3L | 4.6 ± 0.5 | 5.5 ± 0.2* | 7.6 ± 4.8** | 208 ± 182** | 21.4 ± 4.3** |
| 1:7L | 3.9 ± 0.3 | 5.6 ± 0.3* | 8.2 ± 4.6** | 201 ± 188** | 19.3 ± 5.1** |

*p, 0.5 compared to SA,
**$p < 0.001$ compared to SA, 1:1, 3:1 and 7:1

The three-fold and seven-fold dilutions with an extended sonication time produced significantly higher peak videointensity, area under the left ventricular time intensity curve, and transit time when compared to either sonicated albumin and the one-fold, three-fold, and seven-fold dilutions sonicated for 40 seconds.

As can be seen from the above examples, there was significantly better transpulmonary passage with the sonicated mixtures containing albumin and dextrose, e.g, up to between about 1 part of albumin about 3 to 7 parts dextrose. These data suggest that a sonicated multi-fold dilution of albumin with dextrose may be a superior ultrasound contrast agent for clinical applications of contrast echocardiography. The dilutions which appeared to produce the optimal peak videointensity and area under the curve in the left ventricular cavity was the three-fold to seven-fold dilutions of albumin with 50% dextrose. These data demonstrate that only a small quantity of sonicated albumin is required to produce optimal left ventricular opacification following intravenous injection.

EXAMPLE 7

Effect of dextrose concentration on transpulmonary passage of multifold dilutions of sonicated albumin in humans.

Six consecutive 8.0 milliliter intravenous injections of differing dilutions of sterile sonicated solutions of albumin and 50% dextrose (1:1 d50, 1:3 d50, 1:4 d50), albumin and 5% dextrose (1:3 d5, 1:4 d5) and sonicated albumin (SA) alone were given to 8 human volunteers with known cardiac disease. Additionally, a 5.0 milliliter intravenous injection of a four-fold dilution concentrate of albumin and 50% dextrose (1:4 d50C) was given after excess fluid was decanted from the microbubbles. Immediately following each injection, the peak videointensity and area under the curve were measured. Videointensity was plotted as a function of time using on-line digitally acquired videointensity obtained from software supplied in conjunction with the commercially available Hewlett Packard Sonos 1500 Phased Array imaging system (Hewlett Packard, Andover, Mass.). The results are shown in Table 4.

TABLE 4

| Agent | Microbubble Concentration ($\times 10^8$/ml) | Injection volume (ml) | Sonication Time (secs) | PVI | Area |
|---|---|---|---|---|---|
| SA | 3.96 | 8.0 | 40 | 1.5 ± 1.1 | 27 ± 22 |
| 1:1d50 | 5.01 | 8.0 | 70 | 2.3 ± 1.9 | 73 ± 73 |
| 1:3d50 | 4.675 | 8.0 | 80 | 3.0 ± 1.7 | 83 ± 73 |
| 1:4d50 | 4.635 | 8.0 | 80 | 4.6 ± 2.6 | 103 ± 87 |
| 1:3d5 | 4.64 | 8.0 | 80 | 4.7 ± 1.8 | 86 ± 57 |
| 1:4d5 | 4.59 | 8.0 | 80 | 3.4 ± 2.4 | 86 ± 59 |
| 1:4d50 | a. | 5.0 | 80 | 5.2 ± 3.4* | 92 ± 53 |

*p, 0.05 compared to Sonicated Albumin (ANOVA)
a. The microbubble concentration of the concentrated bolus is approximately 5 times greater than the concentration of 4:1d50.

All three-fold and four-fold dilutions of albumin with 50% dextrose or 5% dextrose produced a higher peak videointensity and greater area when compared to sonicated albumin alone or the one-fold (1:1 d50) dilution of albumin with 50% dextrose sonicated for 70 seconds.

As can be seen from Example 7, improved transpulmonary passage can be achieved by using a three-fold or four-fold dilution of albumin with 50% dextrose or 5% dextrose. The dilution which appears to produce the optimal peak videointensity and area under the curve is the four-fold dilution of albumin with 50% dextrose, sonicated for 80 seconds, and concentrated prior to injection. This data demonstrates that a smaller, more compact bolus produces optimal left ventricular opacification.

EXAMPLE 8

Prophetic Study of Peripheral Arterial Structures and Myocardium.

The procedure of Example 7 is repeated except that 16.0 milliliter samples of two-fold to four-fold dilutions of 5% human sonicated albumin with 5% dextrose are employed. These samples are prepared using the sonication technique described in Examples 1–3 and allowed to separate at room temperature. An approximate 2.0 milliliter white layer forms at the top which is the concentrated microbubble layer. The remaining 14 milliliters are decanted. This 2.0 milliliter "compact bolus" is then injected and compared to the 8.0 milliliter injections described in Example 7. In addition to defining myocardial perfusion, carotid artery stenosis, iliac artery stenosis, and renal perfusion are then delineated.

I claim:

1. A method of determining left ventricular videointensity by Echocardiography comprising the following steps:

mixing human serum albumin with a 5% to 50% solution of at least one aqueous monosaccharide in a ratio of 1:3 to 1:7 respectively to form a solution;

sonicating said solution to form microbubbles approximately 3 to 5 microns in diameter, thereby forming an echo contrast agent;

intravenously injecting said echo contrast agent to an animal subject; and detecting the image produced by ultrasound imaging.

2. The method of claim 1 wherein said sonicated mixture is comprised of between about a three-fold and about a ten-fold dilution of about a 5% aqueous solution of human serum albumin with between about a 5% and about a 50% aqueous solution of dextrose.

3. The method of claim 2 wherein said dilution is about three- to four-fold and said dextrose concentration is about a 5% to a 50% solution.

4. An echocardiographic contrast agent comprising a sonicated mixture of a dilution of human serum albumin with aqueous dextrose, so that said mixture is from about 3.75% to about 37.5% by weight of dextrose, said contrast agent being in a pharmaceutically effective dosage form for intravenous or intracoronary injection and having a microbubble concentration of greater than about $4 \times 10^8$/ml, and having microbubbles with an average diameter of 3–5 μm.

5. The contrast agent of claim 4 consisting essentially of a sonicated mixture of about a four-fold dilution of human serum albumin with aqueous dextrose, said contrast agent being in a pharmaceutically effective dosage form for intravenous injection.

6. The contrast agent of claim 4 wherein said mixture comprises between about a 3-fold to about 7-fold dilution of said human serum albumin with about a 5% to about a 50% solution of aqueous dextrose.

7. The contrast agent of claim 4 wherein said mixture comprises about a 3-fold dilution of 50% dextrose.

8. The contrast agent of claim 4 wherein said mixture is about a 3-fold dilution of 5% dextrose.

9. An echocardiographic contrast agent comprising:

a sonicated mixture of a dilution of human serum albumin with aqueous dextrose, said mixture comprising not more than 40% by weight of dextrose, said contrast agent further being in a pharmaceutically-effective dosage form for intravenous or intracoronary injection and having a microbubble concentration of greater than $4 \times 10^8$/ml, and having microbubbles with an average diameter of between 3–5 μm.

10. An echocardiographic contrast agent comprising a sonicated mixture of a three-fold to about a seven-fold dilution of a 5% to 50% solution of human serum albumin with a 5% to 50% solution of an aqueous monosaccharide, so that said mixture is less than 40% by weight of aqueous monosaccharide.

11. The method of claim 1 wherein said human serum albumin is a 5% to 50% solution.

12. A method of determining left ventricular video intensity by echocardiography comprising the following steps:

mixing a 5% to 50% solution of human serum albumin with a 5% to 50% solution of at least one aqueous monosaccharide in a ratio of 1:3 to 1:7 respectively to form a solution;

sonicating said solution to form microbubbles approximately 3 to 5 microns in diameter thereby forming an echo contrast agent;

intravenously injecting said echo contrast agent into an animal subject; and detecting the image produced by ultrasound imaging.

* * * * *